United States Patent
Somasundaram et al.

(10) Patent No.: US 8,644,259 B2
(45) Date of Patent: Feb. 4, 2014

(54) METHODS AND APPARATUS FOR SELECTING OR RESELECTING A HOME NODE-B (CLOSED SUBSCRIBER GROUP (CSG) CELL) AMONG CELLS HAVING COLLIDING PHYSICAL LAYER SIGNALS

(75) Inventors: Shankar Somasundaram, Deer Park, NY (US); Shahrokh Nayeb Nazar, Sainte-Julie (CA); Guodong Zhang, Syosset, NY (US); Rajat P. Mukherjee, Stanford, CA (US)

(73) Assignee: InterDigital Patent Holdings, Inc., Wilmington, DE (US)

( * ) Notice: Subject to any disclaimer, the term of this patent is extended or adjusted under 35 U.S.C. 154(b) by 854 days.

(21) Appl. No.: 12/339,395

(22) Filed: Dec. 19, 2008

(65) Prior Publication Data

US 2009/0168727 A1    Jul. 2, 2009

Related U.S. Application Data

(60) Provisional application No. 61/018,580, filed on Jan. 2, 2008.

(51) Int. Cl.
   *H04W 4/00*        (2009.01)
(52) U.S. Cl.
   USPC ....................................... 370/332; 455/432.1
(58) Field of Classification Search
   USPC ......... 370/331–333, 350, 312, 390, 468, 469; 455/432.1–436, 440, 452.2, 453
   See application file for complete search history.

(56) References Cited

U.S. PATENT DOCUMENTS

| | | | | |
|---|---|---|---|---|
| 7,251,227 | B2 * | 7/2007 | de Jong et al. | 370/331 |
| 7,747,275 | B2 * | 6/2010 | Funnell et al. | 455/525 |
| 2007/0183427 | A1 * | 8/2007 | Nylander et al. | 370/395.2 |
| 2008/0220782 | A1 | 9/2008 | Wang et al. | |
| 2008/0267153 | A1 | 10/2008 | Mukherjee et al. | |

OTHER PUBLICATIONS

Third Generation Partnership Project, "Technical Specification Group Radio Access Network; Evolved Universal Terrestrial Radio Access (E-UTRA); Radio Resource Control (RRC); Protocol Specification (Release 8)", 3GPP TS 36.331, V8.3.0 (Sep. 2007).

Third Generation Partnership Project, "Technical Specification Group Radio Access Network; Physical Layer Procedures (Release 8)", 3GPP TS 36.213, V8.1.0 (Nov. 2007).

Third Generation Partnership Project, "Technical Specification Group Radio Access Network; Evolved Universal Terrestrial Radio Access (E-UTRA) Radio Resource Control (RRC); Protocol Specification (Release 8)", 3GPP TS 36.331 V8.0.0 (Dec. 2007).

(Continued)

*Primary Examiner* — Afshawn Towfighi
(74) *Attorney, Agent, or Firm* — Frank Linguiti

(57) ABSTRACT

A method and apparatus for selecting or reselecting a home Node-B (HNB), (i.e., a closed subscriber group (CSG) cell), among cells having colliding physical layer signals are disclosed. Once the identity (ID) of an HNB is determined, measurements needed to support cell selection or reselection are performed. A broadcast channel that broadcasts an HNB ID is detected and synchronized to, and information obtained from the broadcast channel is forwarded to a non-access stratum (NAS). The broadcasted HNB ID is checked against an HNB white-list provided by the NAS to determine whether the HNB is suitable for a wireless transmit/receive unit (WTRU). The WTRU selects the HNB to camp on, or changes from a cell currently serving the WTRU to the HNB if it is determined to be more suitable than the current serving cell.

16 Claims, 2 Drawing Sheets

(56) References Cited

OTHER PUBLICATIONS

Third Generation Partnership Project, "Technical Specification Group Radio Access Network; Evolved Universal Terrestrial Radio Access (E-UTRA) Radio Resource Control (RRC); Protocol Specification (Release 8)", 3GPP TS 36.331 V8.3.0 (Sep. 2008).
Third Generation Partnership Project, "Technical Specification Group Radio Access Network; Evolved Universal Terrestrial Radio Access (E-UTRA); User Equipment (UE) Procedures in Idle Mode (Release 8)", 3GPP TS 36.211, V8.1.0 (Nov. 2007).
Asustek, "CSG operation handling in IDLE mode," 3GPP TSG-RAN WG2 #59 bis, R2-073941 (Oct. 8-12, 2007).
Ericsson, "Idle state access restriction for home eNB," 3GPP TSG-RAN WG2#59, R2-073415 (Aug. 20-24, 2007).
Motorola, "Layer Identity of CSG Cells," 3GPP TSG-RAN WG2 Meeting #60, R2-075088 (Nov. 5-9, 2007).
Nokia Corporation et al., "CSG Cell Identification for Mobility and Measurement Reporting," 3GPP TSG-RAN WG2 Meeting #59bis, R2-074882 (Nov. 5-9, 2007).
Nokia et al., "Access control for CSG cells," 3GPP TSG-RAN WG2 Meeting #58 bis, R2-072404 (Jun. 25-29, 2007).
Nokia Siemens Networks, "Clean up and update on security, scheduling, mobility, MBMS and DRX," 3GPP TSG-RAN2 Meeting #60, R2-075498 (Nov. 5-9, 2007).
Third Generation Partnership Project, "Technical Specification Group Radio Access Network; Evolved Universal Terrestrial Radio Access (E-UTRA); User Equipment (UE) Procedures in Idle Mode (Release 8)", 3GPP TS 36.304, V8.0.0, (Dec. 2007).
Third Generation Partnership Project, "Technical Specification Group Radio Access Network; Evolved Universal Terrestrial Radio Access (E-UTRA); User Equipment (UE) Procedures in Idle Mode (Release 8)", 3GPP TS 36.304, V8.3.0, (Sep. 2008).
Third Generation Partnership Project, "Technical Specification Group Radio Access Network; Evolved Universal Terrestrial Radio Access (E-UTRA); Physical Channels and Modulation (Release 8)", 3GPP TS 36.211, V8.1.0 (Nov. 2007).
Third Generation Partnership Project, "Technical Specification Group Radio Access Network; Evolved Universal Terrestrial Radio Access (E-UTRA); Physical Channels and Modulation (Release 8)", 3GPP TS 36.211, V8.5.0 (Dec. 2008).
Third Generation Partnership Project, "Technical Specification Group Radio Access Network; Evolved Universal Terrestrial Radio Access (E-UTRA); Radio Resource Control (RRC); Protocol Specification (Release 8)", 3GPP TS 36.331, V8.0.0 (Dec. 2007).
Third Generation Partnership Project, "Technical Specification Group Radio Access Network; Evolved Universal Terrestrial Radio Access (E-UTRA); Radio Resource Control (RRC); Protocol Specification (Release 8)", 3GPP TS 36.331, V8.3.0 (Sep. 2008).
Third Generation Partnership Project, "Technical Specification Group Radio Access Network Physical Layer Procedures (Release 8)", 3GPP TS 36.213, V8.1.0 (Nov. 2007).
Third Generation Partnership Project, "Technical Specification Group Radio Access Network; Physical Layer Procedures (Release 8)", 3GPP TS 36.213, V8.4.0 (Sep. 2008).
Third Generation Partnership Project, "Technical Specification Group Radio Access Network; Evolved Universal Terrestrial Radio Access (E-UTRA)and Evolved Universal Terrestrial Radio Access Network (E-UTRAN); Overall description; Stage 2 (Release 8)," 3GPP TS 36.300, V8.2.0 (Sep. 2007).
Third Generation Partnership Project, "Technical Specification Group Radio Access Network; User Equipment (UE) procedures in idle mode and procedures for cell reselection in connected mode(Release 1999)," 3GPP TS 25.304, V3.14.0 (Mar. 2004).
Third Generation Partnership Project, "Technical Specification Group Radio Access Network; User Equipment (UE) procedures in idle mode and procedures for cell reselection in connected mode (Release 4)," 3GPP TS 25.304, V4.8.0 (Mar. 2004).
Third Generation Partnership Project, "Technical Specification Group Radio Access Network; User Equipment (UE) procedures in idle mode and procedures for cell reselection in connected mode (Release 5)," 3GPP TS 25.304 V5.9.0 (Sep. 2005).
Third Generation Partnership Project, "Technical Specification Group Radio Access Network; User Equipment (UE) procedures in idle mode and procedures for cell reselection in connected mode (Release 6)," 3GPP TS 25.304 V6.9.0 (Mar. 2006).
Third Generation Partnership Project, "Technical Specification Group Radio Access Network; User Equipment (UE) procedures in idle mode and procedures for cell reselection in connected mode (Release 6)," 3GPP TS 25.304 V6.10.0 (Mar. 2008).
Third Generation Partnership Project, "Technical Specification Group Radio Access Network; User Equipment (UE) procedures in idle mode and procedures for cell reselection in connected mode (Release 7)," 3GPP TS 25.304 V7.3.0 (Sep. 2007).
Third Generation Partnership Project, "Technical Specification Group Radio Access Network; User Equipment (UE) procedures in idle mode and procedures for cell reselection in connected mode (Release 7)," 3GPP TS 25.304 V7.7.0 (Sep. 2008).
Third Generation Partnership Project, "Technical Specification Group Radio Access Network; User Equipment (UE) procedures in idle mode and procedures for cell reselection in connected mode (Release 8)," 3GPP TS 25.304 V8.0.0 (Dec. 2007).
Third Generation Partnership Project, "Technical Specification Group Radio Access Network; User Equipment (UE) procedures in idle mode and procedures for cell reselection in connected mode (Release 8)," 3GPP TS 25.304 V8.3.0 (Sep. 2008).
Third Generation Partnership Project, "Technical Specification Group Radio Access Network; Evolved Universal Terrestrial Radio Access (E-UTRA) and Evolved Universal Terrestrial Radio Access Network (E-UTRAN); Overall description; Stage 2 (Release 8)," 3GPP TS 36.300 V8.3.0 (Dec. 2007).
Third Generation Partnership Project, "Technical Specification Group Radio Access Network; Evolved Universal Terrestrial Radio Access (E-Utra) and Evolved Universal Terrestrial Radio Access Network (E-Utran); Overall description; Stage 2 (Release 8)," 3GPP TS 36.300 V8.6.0 (Sep. 2008).
TSG RAN WG2, "LS on CSG Cells Handling," 3GPP TSG-RAN WG2 Meeting #59, R2-073740 (Aug. 20-24, 2007).

* cited by examiner

METHODS AND APPARATUS FOR SELECTING OR RESELECTING A HOME NODE-B (CLOSED SUBSCRIBER GROUP (CSG) CELL) AMONG CELLS HAVING COLLIDING PHYSICAL LAYER SIGNALS

CROSS REFERENCE TO RELATED APPLICATION

This application claims the benefit of U.S. Provisional Application No. 61/018,580 filed Jan. 2, 2008, which is incorporated by reference as if fully set forth.

FIELD OF DISCLOSURE

This application is related to wireless communications.

BACKGROUND

Efforts are currently being made for the Third Generation Partnership Project (3GPP) long term evolution (LTE) program to introduce new technology, new architecture and new LTE settings and configurations in order to provide improved spectral efficiency, reduced latency, and improved utilization of radio resources to provide faster user experiences and richer applications and services at a lower cost.

As part of these efforts, the 3GPP LTE program is working on introducing the concept of a home evolved Node-B (HNB) in LTE, (and also, possibly in a parallel fashion, in Release 8 wideband code division multiple access (WCDMA), global system for mobile communications (GSM) enhanced data rates for GSM evolution (EDGE) radio access network (GE-RAN) and other cellular standards). The HNB is intended to be similar to a wireless local area network (WLAN) access point (AP), and is to be designed in a manner that allows access to cellular services to users over extremely small service areas, (e.g., homes or small offices). This can be particularly useful in areas where cellular networks have not been deployed and/or legacy radio access technology (RAT) coverage exists, as well as in areas where cellular coverage may be faint or non-existent for radio related reasons, (e.g., an underground metro or shopping mall). The subscriber, (e.g., an individual or an organization), may deploy an HNB over an area where such service is desired.

An HNB in an LTE network may be identified by means of a unique tracking area (TA) identity (ID), cell ID, or a combination of both. The problem that may be encountered with this approach is that in order to read the ID of a cell, a wireless transmit/receive unit (WTRU) has to acquire the cell broadcast information of the HNB. However, when the WTRU is in a connected mode while performing measurements, the WTRU does not usually read the radio resource control (RRC) layer broadcast channel. However, if the WTRU were to do so, it might lead to unacceptable performance requirements since there may be many HNBs in the vicinity.

One possible solution is that HNBs be identified at the physical (PHY) layer by means of a reserved physical layer synchronization signal. In LTE, there are three possible primary synchronization channels (P-SCH) and 170 possible secondary synchronization channels (S-SCH), for a total of 510 unique physical layer cell IDs. However, a problem with this solution is that the PHY layer cell ID of two or more HNBs may collide, and the WTRU may not be able to distinguish between them.

In earlier systems, cell planning techniques were sufficient to ensure that there was no collision between neighboring cells of different operators. However, with potentially hundreds of HNBs in the vicinity of the WTRU, (belonging to potentially multiple operators), cell planning techniques may be less effective. In such a scenario, it becomes necessary to address the issue of WTRU procedures when a collision between neighboring cells is detected.

SUMMARY

A method and apparatus for selecting or reselecting an HNB, (i.e., a closed subscriber group (CSG) cell), among cells having colliding physical layer signals are disclosed. Once the identity (ID) of an HNB is determined, measurements needed to support cell selection or reselection are performed. A broadcast channel that broadcasts an HNB ID is detected and synchronized to, and information obtained from the broadcast channel is forwarded to a non-access stratum (NAS). The broadcasted HNB ID is checked against an HNB white-list provided by the NAS to determine whether the HNB is suitable for a WTRU to camp on. The WTRU selects the HNB to camp on, or changes from a cell currently serving the WTRU to the HNB if it is determined to be more suitable than the current serving cell.

BRIEF DESCRIPTION OF THE DRAWINGS

A more detailed understanding may be had from the following description, given by way of example and to be understood in conjunction with the accompanying drawings wherein:

FIG. 1 shows a WTRU in communication with a cell that potentially may be suitable for the WTRU to camp on.

DETAILED DESCRIPTION

Figure 1:
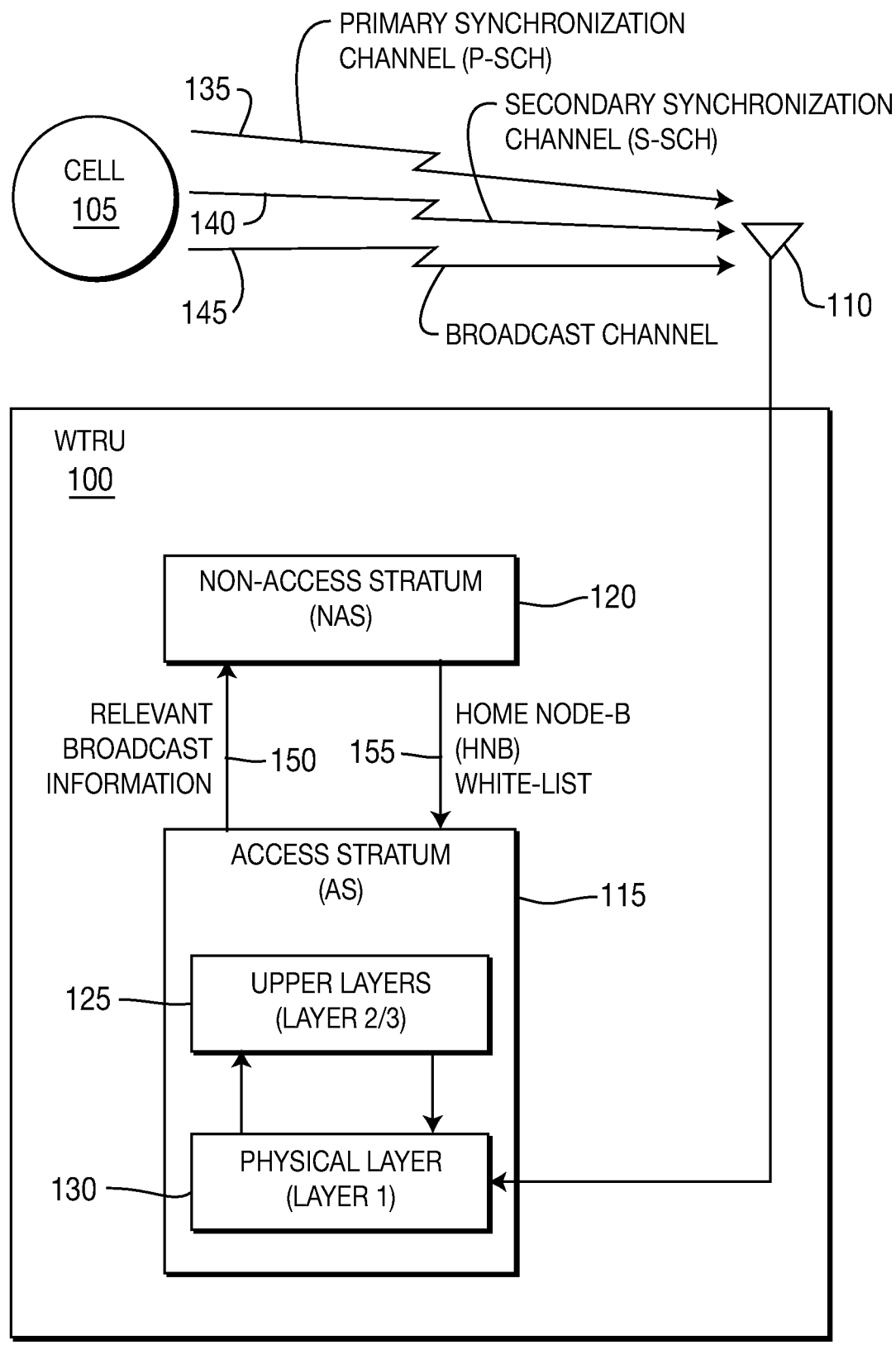

When referred to hereafter, the terminology "wireless transmit/receive unit (WTRU)" includes but is not limited to a user equipment (UE), a mobile station, a fixed or mobile subscriber unit, a pager, a cellular telephone, a personal digital assistant (PDA), a computer, or any other type of user device capable of operating in a wireless environment.

When referred to hereafter, the terminology "base station" includes but is not limited to a Node-B, an evolved or E-UT-RAN Node-B (eNodeB), a site controller, an access point (AP), or any other type of interfacing device capable of operating in a wireless environment.

Hereafter, the terms home Node-B (HNB) and closed subscriber group (CSG) are equivalent. Although this application describes features from the perspective of collision detection and resolution of HNB physical (PHY) layer IDs, they are applicable to the collision detection and resolution of any cells (e.g., macrocells). These concepts are applicable to various wireless standards, such as WCDMA, GSM, IEEE 802.16 wireless metropolitan area networks (WiMAX), and the like.

The white-list of HNBs that the network configures the WTRU with may include the PHY layer ID of the HNB to which the WTRU has access, such as a primary synchronization channel (P-SCH), a secondary synchronization channel (S-SCH), some other ID, or a combination thereof. Additionally, the white-list includes any upper layer ID of those HNBs, such as a tracking area (TA) ID, a cell ID, a CSG ID, some other ID or a combination thereof. This PHY layer ID may belong to one of many reserved for HNB access. A WTRU that detects a P-SCH/S-SCH which belongs to this reserved list would know immediately that it has detected an HNB.

Certain physical layer IDs are reserved for "public" HNBs and others are reserved for "private" HNBs.

When a cell has been determined by the WTRU to be an HNB, layer 1 (i.e., a PHY layer) of an access stratum (AS) in the WTRU forwards relevant broadcast information, (e.g., management information field (MIB), SU-1, or the like), received from the cell to upper layers (i.e., layer 2/3) in the AS, as well as to a non-access stratum (NAS) in the WTRU. For example, a primitive may be used to indicate that the cell is an HNB. Optionally, the PHY layer may distinguish if the HNB is a "public" HNB or a "private" HNB to the upper layers.

The function of the AS is to support the NAS. This includes the functions and protocols for the transport of information across the UTRAN and air interface. The NAS is responsible for different aspects like call control, mobility management, session management and the like.

An additional identification of the HNB may be carried on the downlink physical channels of the HNB, such as by allocating a few bits that may be carried on any physical channel, (e.g., physical broadcast channel (P-BCH), common control physical channel (CCPCH)). This additional identification of the HNB may also be configured in the WTRU as part of its white-list, and may be used by the WTRU to resolve a collision in case it detects a collision in the P-SCH/S-SCH.

When the WTRU is in an idle mode, as part of a cell selection/reselection procedure, and the WTRU detects multiple instances of the PHY layer HNB IDs that the WTRU has access to, (e.g., using a white-list), the WTRU may perform any or all of the following in any combination.

The WTRU may provide an indication of the collision to upper layers, (e.g., radio resource controller (RRC)), and optionally provide an indication to the upper layers about the scale of the collision (e.g., three identical signals are detected).

For each of the PHY layer IDs, the WTRU may proceed to make measurements on a reference symbol, acquire at least one broadcast channel and pass this information to the upper layers. The upper layers may resolve the collision by checking the upper layer identification of the HNBs, (e.g., TA ID, CSG ID, cell ID, some other ID or combination of the above). If the HNB meets the criteria for cell selection/reselection, which may be determined by the measurements and access parameters, then the upper layers may pass the information about the selected HNB back to the PHY layer to allow the PHY layer to perform its own procedures for camping on the particular cell. For this purpose, the PHY layer may maintain an ordered list or memorize the order of the collision.

In addition, the upper layers may instruct layer 1 as to how many broadcast channels to acquire, and/or how many measurements to make (e.g., acquire the x strongest of the y cells for which collision is detected, where $x \leq y$).

Optionally, the above procedures may only be performed by the layer 1 and upper layers for the cells for which collision is detected and meet some other criteria, (e.g., some basic radio related criteria such as cell selection criteria S or equivalent for HNBs). Use of any additional identification of the HNB that may be carried on the downlink physical channels of the HNB to resolve the collision When the WTRU is in a connected mode, and the WTRU detects multiple instances of the PHY layer HNB ID that belong to the list of cell IDs of interest and the WTRU has access to, (e.g., using white-list), the WTRU may perform any or all of the following in any combination.

The WTRU may provide an indication of the collision to upper layers and optionally provide an indication to the upper layers about the scale of the collision, (e.g., three identical signals are detected). For each of the PHY layer IDs, the WTRU proceeds to make measurements on a reference symbol and acquire the broadcast channels and pass this information to upper layers. The upper layers may resolve the collision by checking the upper layer identification of the HNBs, (e.g., TA ID, CSG ID, cell ID, some other ID or combination thereof). The upper layers may report the measurements of only those cells which it has access to. The upper layers may pass the information about the selected HNB back to the PHY layer to allow the PHY layer to "remember" the particular cell in case of a future handover. For this purpose, the PHY layer may maintain an ordered list or memorize the order of the collision.

The upper layer (e.g., RRC) may instruct the PHY layer of how many broadcast channels to acquire and/or how many measurements to make (e.g., acquire the x strongest of the y cells for which collision is detected where $x \leq y$).

Optionally, the above procedures may only be performed by the PHY and upper layers for the cells for which collision is detected and meet some criteria (e.g., some basic radio related criteria such as cell selection criteria S or equivalent for HNBs). The upper layers may provide an indication to the network, (e.g., in the measurement report) that a collision was detected. Any additional parameters such as the scale of the collision, (e.g., three identical signals are detected), may be provided. The network may use this information to configure a longer measurement gap which may allow the WTRU to resolve the collision, (e.g., by checking upper layer identification of the HNB). The network may instruct the WTRU to move to idle mode and then select the cell. This command may be implemented either immediately or at a future instance of time as indicated by the network (e.g., transmission timing intervals (TTIs), system frame numbers (SFNs)).

The WTRU may use any additional identification of the HNB that may be carried on the downlink physical channels of the HNB to resolve the collision.

FIG. 1 shows a WTRU 100 in communication with a cell 105 that potentially may be suitable for the WTRU to camp on. The WTRU may include an antenna 110, an AS 115 and a NAS 120. The AS 115 may include upper layers 125 (layer 2/3) and a PHY layer 130 (layer 1).

Figure 2:
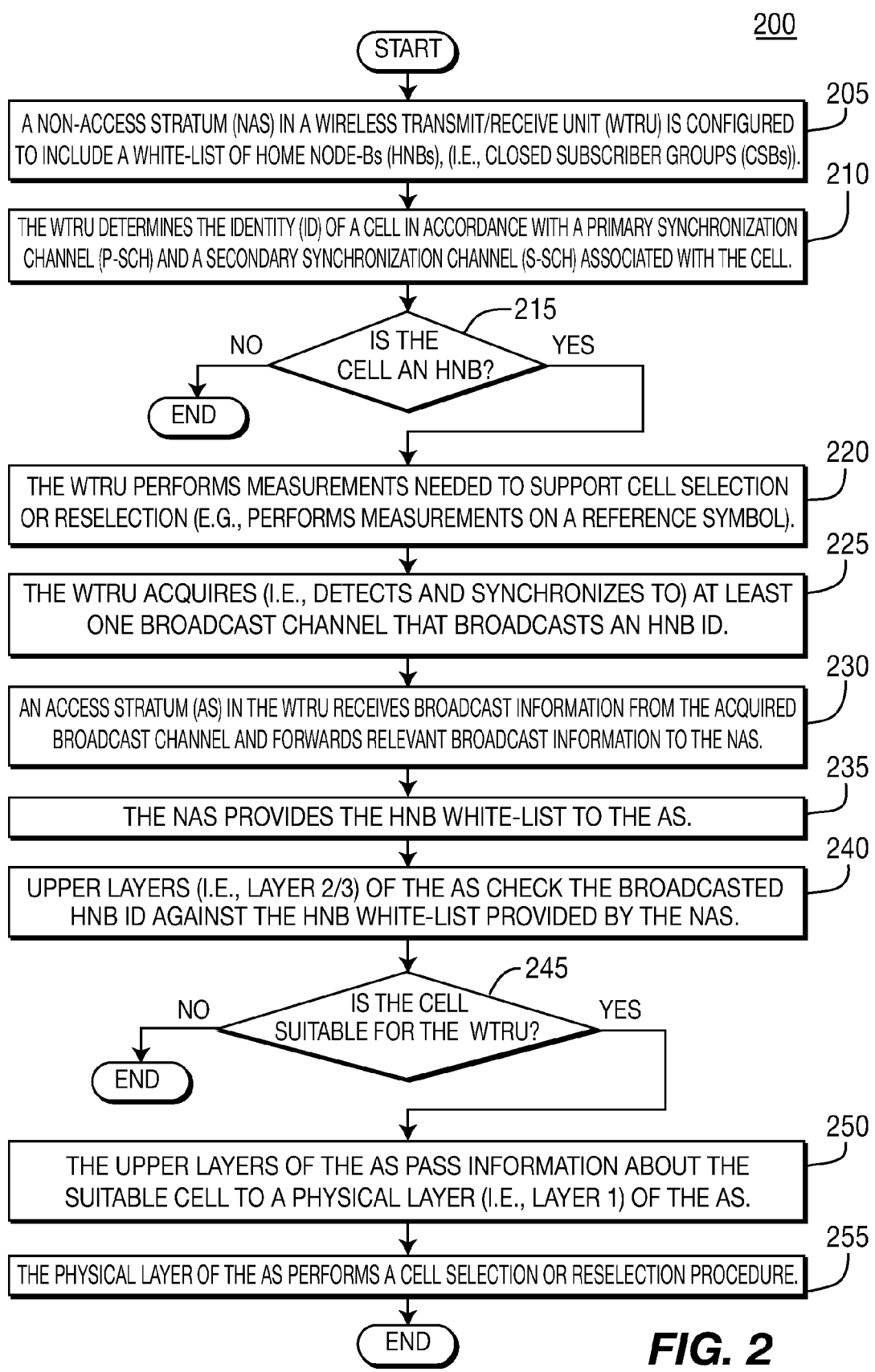
FIG. 2 is a flow diagram of a procedure for selecting or reselecting an HNB among colliding cells.

FIG. 2 is a flow diagram of a procedure 200 for selecting or reselecting an HNB among colliding cells. Referring to FIGS. 1 and 2, in step 205, the NAS 120 in the WTRU 100 is configured to include a white-list of HNBs (i.e., CSGs). In step 210, the WTRU 100 determines the ID of a cell 105 in accordance with a P-SCH 135 and an S-SCH 140 associated with the cell 105. In step 215, a determination is made as to whether the cell is an HNB (i.e., CSG cell). If the cell 105 is not an HNB, the procedure 200 terminates. If the cell 105 is an HNB, the WTRU 100 performs measurements needed to support cell selection or reselection (e.g., performs measurements on a reference symbol) in step 220. In step 225, the WTRU 100 acquires (i.e., detects and synchronizes to) at least one broadcast channel 145 that broadcasts an HNB ID. In step 230, the AS 115 in the WTRU 100 receives broadcast information from the acquired broadcast channel and forwards relevant broadcast information to the NAS 120. In step 235, the NAS 120 provides the HNB white-list to the AS 115. In step 240, the upper layers 125 (i.e., layer 2/3) of the AS check the broadcasted HNB ID against the HNB white-list provided by the NAS 120. In step 245, a determination is made as to whether the cell 105 is suitable for the WTRU 100 to camp on. If the cell 105 is not suitable, the procedure 200 terminates. If the cell 105 is suitable, the upper layers 125 of the AS 115 pass information about the suitable cell to the physical layer 130 of the AS 115 (step 250). Finally, in step 255, the physical layer 130 of the AS 115 performs a cell selection or reselection procedure. If a cell selection procedure is performed, the WTRU 100 selects the suitable cell to camp on. If a cell reselection procedure is performed, the WTRU 100 changes a cell that is currently serving the WTRU 100 to the suitable cell if the suitable cell is determined to be more suitable than the cell that is currently serving the WTRU.

Although features and elements are described above in particular combinations, each feature or element can be used alone without the other features and elements or in various combinations with or without other features and elements. The methods or flow charts provided herein may be implemented in a computer program, software, or firmware incorporated in a computer-readable storage medium for execution by a general purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine.

A processor in association with software may be used to implement a radio frequency transceiver for use in a wireless transmit receive unit (WTRU), user equipment (UE), terminal, base station, radio network controller (RNC), or any host computer. The WTRU may be used in conjunction with modules, implemented in hardware and/or software, such as a camera, a video camera module, a videophone, a speakerphone, a vibration device, a speaker, a microphone, a television transceiver, a hands free headset, a keyboard, a Bluetooth® module, a frequency modulated (FM) radio unit, a liquid crystal display (LCD) display unit, an organic light-emitting diode (OLED) display unit, a digital music player, a media player, a video game player module, an Internet browser, and/or any wireless local area network (WLAN) or Ultra Wide Band (UWB) module.

What is claimed is:

1. A method, implemented by a wireless transmit/receive unit (WTRU), of reselecting a closed subscriber group (CSG) among cells having colliding physical layer signals, the method comprising:
    performing measurements needed to support cell reselection;
    receiving a CSG cell identity (ID) from a CSG cell;
    a non-access stratum (NAS) in the WTRU providing a CSG white-list to an access stratum (AS) in the WTRU;
    the AS checking the CSG cell ID against the CSG white-list to determine whether the CSG cell is suitable for the WTRU; and
    performing a cell reselection to the CSG cell on a condition that the CSG cell is suitable.

2. The method of claim 1 wherein the CSG cell ID is determined in accordance with a primary synchronization channel (P-SCH) and a secondary synchronization channel (S-SCH) associated with the CSG cell.

3. The method of claim 1 wherein the measurements performed to support cell reselection include measurements performed on a reference symbol.

4. The method of claim 1 further comprising:
    upper layers of the AS passing information about the suitable CSG cell to a physical layer of the AS; and
    a physical layer of the AS performing the cell reselection procedure to change from a cell that is currently serving the WTRU to the CSG cell.

5. A wireless transmit/receive unit (WTRU) for reselecting a closed subscriber group (CSG) cell among cells having colliding physical layer signals, the WTRU comprising:
    an access stratum (AS); and
    a non-access stratum (NAS) configured to provide a CSG white-list to the AS,
    wherein the WTRU is configured to:
        perform measurements needed to support cell reselection;
        receive a CSG cell identity (ID) from a CSG cell;
        use the AS to check the CSG cell ID against the CSG white-list to determine whether the CSG cell is suitable for the WTRU; and
        perform a cell reselection to the CSG cell on a condition that the CSG cell is suitable.

6. The WTRU of claim 5 wherein the CSG cell ID is determined in accordance with a primary synchronization channel (P-SCH) and a secondary synchronization channel (S-SCH) associated with the CSG cell.

7. The WTRU of claim 5 wherein the measurements performed to support cell reselection include measurements performed on a reference symbol.

8. The WTRU of claim 5 wherein the AS comprises upper layers and a physical layer, wherein the upper layers are configured to pass information about the suitable CSG cell to the physical layer of the AS, and the physical layer is configured to perform the cell reselection procedure to change from a cell that is currently serving the WTRU to the CSG cell.

9. A method, implemented by a wireless transmit/receive unit (WTRU), of selecting a closed subscriber group (CSG) among cells having colliding physical layer signals, the method comprising:
    performing measurements needed to support cell selection;
    receiving a CSG cell identity (ID) from a CSG cell;
    a non-access stratum (NAS) in the WTRU providing a CSG white-list to an access stratum (AS) in the WTRU;
    the AS checking the CSG cell ID against the CSG white-list to determine whether the CSG cell is suitable for the WTRU; and
    performing a cell selection procedure to select a suitable CSG cell to camp on.

10. The method of claim 9 wherein the CSG cell ID is determined in accordance with a primary synchronization channel (P-SCH) and a secondary synchronization channel (S-SCH) associated with the CSG cell.

11. The method of claim 9 wherein the measurements performed to support cell selection include measurements performed on a reference symbol.

12. The method of claim 9 further comprising:
    upper layers of the AS passing information about the suitable CSG cell to a physical layer of the AS; and
    a physical layer of the AS performing the cell selection procedure to select the suitable CSG cell.

13. A wireless transmit/receive unit (WTRU) for selecting a closed subscriber group (CSG) cell among cells having colliding physical layer signals, the WTRU comprising:
    an access stratum (AS); and
    a non-access stratum (NAS) configured to provide a CSG white-list to the AS, wherein the WTRU is configured to:
  perform measurements needed to support cell selection;
  receive a CSG cell identity (ID) from a CSG cell;
  use the AS to check the CSG cell ID against the CSG white-list to determine whether the CSG cell is suitable for the WTRU; and
  perform a cell selection procedure to select a suitable CSG cell to camp on.

14. The WTRU of claim 13 wherein the CSG cell ID is determined in accordance with a primary synchronization channel (P-SCH) and a secondary synchronization channel (S-SCH) associated with the CSG cell.

15. The WTRU of claim 13 wherein the measurements performed to support cell selection include measurements performed on a reference symbol.

16. The WTRU of claim 13 wherein the AS comprises upper layers and a physical layer, wherein the upper layers are configured to pass information about the suitable CSG cell to the physical layer of the AS, and the physical layer is configured to perform the cell selection procedure to select the suitable CSG cell.

* * * * *

UNITED STATES PATENT AND TRADEMARK OFFICE
CERTIFICATE OF CORRECTION

| | | |
|---|---|---|
| PATENT NO. | : 8,644,259 B2 | Page 1 of 1 |
| APPLICATION NO. | : 12/339395 | |
| DATED | : February 4, 2014 | |
| INVENTOR(S) | : Somasundaram et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 984 days.

Signed and Sealed this
First Day of September, 2015

Michelle K. Lee
*Director of the United States Patent and Trademark Office*